(12) United States Patent
Sinha et al.

(10) Patent No.: US 12,127,972 B2
(45) Date of Patent: Oct. 29, 2024

(54) CANNULAS FOR OPHTHALMIC PROCEDURES

(71) Applicant: Alcon Inc., Fribourg (CH)

(72) Inventors: Ashish Sinha, Irvine, CA (US); Robert Jeffrey Heng, Lake Forest, CA (US)

(73) Assignee: Alcon Inc., Fribourg (CH)

( * ) Notice: Subject to any disclaimer, the term of this patent is extended or adjusted under 35 U.S.C. 154(b) by 86 days.

(21) Appl. No.: 17/805,896

(22) Filed: Jun. 8, 2022

(65) Prior Publication Data

US 2023/0022895 A1     Jan. 26, 2023

Related U.S. Application Data

(60) Provisional application No. 63/223,645, filed on Jul. 20, 2021.

(51) Int. Cl.
*A61F 9/00* (2006.01)
*A61F 9/007* (2006.01)

(52) U.S. Cl.
CPC ............ *A61F 9/0008* (2013.01); *A61F 9/007* (2013.01); *A61B 2217/007* (2013.01)

(58) Field of Classification Search
CPC .... A61F 9/0008; A61F 9/007; A61F 9/00781; A61F 9/00736; A61B 2217/007; A61B 2017/3433; A61B 17/3421; A61M 3/0279
See application file for complete search history.

(56) References Cited

U.S. PATENT DOCUMENTS

| | | | |
|---|---|---|---|
| 4,551,129 A | 11/1985 | Coleman | |
| 5,201,730 A | 4/1993 | Easley | |
| 5,275,593 A | 1/1994 | Easley et al. | |
| 5,407,441 A * | 4/1995 | Greenbaum | A61F 9/0008 604/294 |
| 5,437,644 A * | 8/1995 | Nobles | A61M 25/0102 604/164.11 |
| 5,478,338 A | 12/1995 | Reynard | |
| 5,591,160 A | 1/1997 | Reynard | |
| 5,651,783 A | 7/1997 | Raynard | |
| 6,290,690 B1 | 9/2001 | Huculak | |

(Continued)

FOREIGN PATENT DOCUMENTS

| | | |
|---|---|---|
| CN | 111870324 A | 11/2020 |
| WO | 2022075840 A2 | 4/2022 |

OTHER PUBLICATIONS

Alcon Surgical Retina Product Catalog, V4, 2019, pp. 3-10.

(Continued)

*Primary Examiner* — Kai H Weng
*Assistant Examiner* — Alessandro R Del Priore (57) ABSTRACT

Certain aspects of the present disclosure generally relate to ophthalmic surgery, and more particularly, to methods and apparatuses for controlling intraocular pressure (IOP) and administering ocular tamponades during or after ophthalmic surgery. An exemplary apparatus generally includes a proximal segment having a first inner diameter (ID), a first proximal end, and a first distal end. The apparatus further includes a distal segment having a second ID smaller than the first ID, a second proximal end, and a second distal end configured to be disposed inside a hub or a cannula transition of a valved cannula comprising the hub, a shaft, and the cannula transition between the hub and the shaft.

8 Claims, 8 Drawing Sheets

(56) References Cited

U.S. PATENT DOCUMENTS

| | | |
|---|---|---|
| 6,302,873 B1 | 10/2001 | Moenning |
| 6,439,541 B1 * | 8/2002 | Nosel ................ A61B 17/3498 |
| | | 251/149.1 |
| 6,740,064 B1 | 5/2004 | Sorrentino et al. |
| 7,390,317 B2 * | 6/2008 | Taylor ................ A61B 17/3498 |
| | | 606/167 |
| 7,783,346 B2 | 8/2010 | Smith et al. |
| 7,846,134 B1 | 12/2010 | Nadolski |
| 8,251,980 B2 | 8/2012 | Zica |
| 8,277,418 B2 | 10/2012 | Lopez |
| 8,343,106 B2 | 1/2013 | Lopez et al. |
| 8,888,692 B1 | 11/2014 | Pravongviengkham et al. |
| 8,900,139 B2 | 12/2014 | Yadlowsky |
| 8,968,347 B2 | 3/2015 | McCollam |
| 9,055,885 B2 | 6/2015 | Horvath |
| 9,066,678 B2 | 6/2015 | Auld |
| 9,089,364 B2 | 7/2015 | Bhadri |
| 9,198,797 B2 | 12/2015 | Kerns |
| 9,364,982 B2 | 6/2016 | Schaller |
| 9,402,643 B2 | 8/2016 | Auld |
| 9,561,085 B2 | 2/2017 | Yadlowsky |
| 9,693,802 B2 | 7/2017 | Evans et al. |
| 9,775,642 B2 | 10/2017 | Azarbarzin et al. |
| 9,839,749 B2 | 12/2017 | Johnson |
| 9,956,053 B2 | 5/2018 | Diao |
| 10,016,248 B2 | 7/2018 | Mirsepassi |
| 10,039,669 B2 | 8/2018 | Heeren |
| 10,244,931 B2 | 4/2019 | Kern |
| 10,307,290 B2 | 6/2019 | Kern |
| 10,376,414 B2 | 8/2019 | Hallen |
| 10,610,408 B2 | 4/2020 | Farley |
| 10,905,462 B2 | 2/2021 | Ochoa |
| 10,987,247 B2 | 4/2021 | Moreno et al. |
| 11,071,566 B2 | 7/2021 | Brannan |
| 11,166,843 B2 | 11/2021 | Hallen |
| 11,382,659 B2 | 7/2022 | Pravong et al. |
| 11,395,713 B2 | 7/2022 | Grueebler et al. |
| 2008/0097346 A1 | 4/2008 | Charles |
| 2008/0172009 A1 | 7/2008 | Attinger |
| 2008/0177239 A1 * | 7/2008 | Li ...................... A61B 17/3421 |
| | | 604/264 |
| 2008/0281277 A1 * | 11/2008 | Thyzel ................ A61F 9/007 |
| | | 604/256 |
| 2009/0076463 A1 * | 3/2009 | Attinger ............. A61B 17/3421 |
| | | 604/264 |
| 2009/0161384 A1 | 6/2009 | Smith |
| 2009/0234292 A1 | 9/2009 | Di Nardo |
| 2011/0152774 A1 * | 6/2011 | Lopez ................. A61F 9/007 |
| | | 604/167.01 |
| 2014/0121469 A1 | 5/2014 | Meckel et al. |
| 2016/0302878 A1 | 10/2016 | Kern |
| 2017/0014023 A1 | 1/2017 | Kern |
| 2017/0014267 A1 | 1/2017 | Kern |
| 2017/0119491 A1 | 5/2017 | Mirsepassi |
| 2017/0165114 A1 | 6/2017 | Hallen |
| 2018/0055596 A1 | 3/2018 | Johnson |
| 2018/0104423 A1 | 4/2018 | Minnelli et al. |
| 2018/0132963 A1 | 5/2018 | Diao |
| 2018/0133057 A1 | 5/2018 | Diao |
| 2018/0168768 A1 | 6/2018 | Mirsepassi |
| 2018/0168861 A1 | 6/2018 | Mirsepassi |
| 2018/0338776 A1 | 11/2018 | Farley |
| 2018/0338859 A1 | 11/2018 | Mirsepassi |
| 2018/0338860 A1 | 11/2018 | Farley |
| 2019/0239979 A1 | 8/2019 | Abt |
| 2019/0307527 A1 | 10/2019 | Grueebler |
| 2019/0374248 A1 | 12/2019 | Grueebler |
| 2020/0022773 A1 | 1/2020 | Grueebler |
| 2020/0337722 A1 | 10/2020 | Charles |
| 2020/0337901 A1 | 10/2020 | Charles |

OTHER PUBLICATIONS

U.S. Appl. No. 18/411,341, filed Jan. 12, 2024 with a priority date of Jan. 18, 2023 (based on U.S. Appl. No. 63/480,341) (32 pages).

* cited by examiner

| Reference Numeral | Dimension |
|---|---|
| 206A | ø.040 |
| 206B | ø.021 |
| 208A | ø.016 |
| 234 | .075 |
| 235 | .0427 |
| 236 | .035 |
| 238 | ø.002 |
| 240 | ø.086 |
| 242 | ø.023 |
| 244 | .0507 |
| 246 | .156 |
| 247 | ø.126 |

| Reference Numeral | Dimension |
|---|---|
| 306A | ø.044 |
| 306B | ø.016 |
| 307A | ø.022 |
| 307B | ø.022 |
| 308A | ø.012 |
| 334 | .075 |
| 335 | .044 |
| 336 | .035 |
| 340 | ø.086 |
| 342 | ø.015 |
| 344 | .098 |
| 346 | .203 |
| 347 | ø.126 |
| 348 | ø.023 |

| Reference Numeral | Dimension |
|---|---|
| 406A | ⌀.195 |
| 407A | ⌀.015 |
| 407B | ⌀.021 |
| 408A | ⌀.195 |
| 434 | .075 |
| 435 | .044 |
| 436 | 0.050 |
| 440 | ⌀.086 |
| 442 | ⌀.015 |
| 444 | .098 |
| 446 | 0.338 |
| 447 | ⌀.092 |
| 448 | ⌀.023 |
| 452 | 161° |

FIG. 4C

CANNULAS FOR OPHTHALMIC PROCEDURES

PRIORITY CLAIM

This application claims the benefit of priority of U.S. Provisional Patent Application Ser. No. 63/223,645 titled "CANNULAS FOR OPHTHALMIC PROCEDURES," filed on Jul. 20, 2021, whose inventors are Ashish Sinha and Robert Jeffrey Heng, which is hereby incorporated by reference in its entirety as though fully and completely set forth herein.

FIELD OF THE INVENTION

The present disclosure relates generally to devices, systems, and methods to control intraocular pressure (IOP) and/or administer ocular tamponades, such as during or after ophthalmic surgery. More particularly, the present disclosure relates to ophthalmic cannulas, such as infusion cannulas and injection cannulas, and methods of use thereof.

BACKGROUND

Posterior segment surgical procedures are performed to treat conditions of the back of the eye, such as age-related macular degeneration (AMD), diabetic retinopathy and diabetic vitreous hemorrhage, macular hole, retinal detachment, epiretinal membrane, cytomegalovirus (CMV) retinitis, and others.

Certain problems affecting the back of the eye may require a vitrectomy, or surgical removal of the vitreous, which is a normally clear, gel-like substance that fills the center of the eye helping to provide form and shape to the eye. For example, a vitrectomy may be performed to clear blood and debris from the eye, to remove scar tissue, or to alleviate traction on the retina. During the procedure, three separate incisions are made in the pars plana of the eye, which is located just behind the iris but in front of the retina. The incisions are used to pass instruments into the eye such as a light pipe, an infusion port, and/or a vitrectomy cutting device. A valved cannula is positioned within each incision to enable instrument access via the cannula into the eye while, at the same time, providing a self-sealing valve to passively control fluid and pressure communication between inside and outside the eye via the cannula.

As vitreous fluid is aspirated during posterior segment surgery, intraocular pressure (IOP) decreases and the patient's eye tends to soften. An infusion cannula may be coupled to the valved cannulas to infuse fluid, such as liquid or gas (e.g., balanced salt solution (BSS)), to the eye to maintain IOP and avoid globe deformation or collapse. In addition, maintaining IOP may help maintain scleral rigidity to facilitate movement of the eye and exchange of instruments during the procedure. However, IOP must be carefully regulated, as prolonged periods of elevated IOP can damage eye structures. If IOP becomes too high, another infusion cannula may be used to vent fluid from the eye to relieve pressure.

In another example, an injection cannula may be coupled to the valved cannula and used to inject a viscous fluid into the ocular space, such as an ocular tamponade for preventing fluid flow through a retinal break. The tamponade may replace vitreous removed during a vitrectomy and may be a gas or a solution (e.g., silicone oil). After the procedure, the tamponade may remain in the patient's eye for a period of time, after which it may be extracted.

Conventional fluid cannulas (e.g., infusion cannulas, injection cannulas, etc.) have various drawbacks. For example, conventional fluid cannulas are typically size specific, wherein each fluid cannula has dimensions tailored to a particular gauge of valved cannula to which the fluid cannula is to be coupled. Valved cannulas are available in several different gauges (e.g., 23 gauge, 25 gauge, and 27 gauge), and thus a user (e.g., an ophthalmic surgeon) must have available a fluid cannula specifically sized to the desired valved cannula gauge for a surgical procedure. Using different sized valved cannulas adds inconvenience to the procedure. Furthermore, conventional fluid cannula designs create relatively high fluidic friction of fluids passing therethrough. The high fluidic friction restricts overall fluid flow and requires higher pressures to maintain a given fluid flow rate. Operating at higher pressures may require larger pumps and may cause additional wear and tear on the equipment. In certain examples, due to the limitations of traditional tubing sets and viscous fluid delivery systems at high pressures, burst failure and disconnection thereof may occur. Furthermore, operating at lower pressures minimizes the risk of harm to ocular tissue.

Therefore, there is a need for improved devices, systems, and methods for controlling IOP and administering fluids, and there is a particular need for improved fluid cannulas that address at least some of the drawbacks described above.

BRIEF SUMMARY

The present disclosure relates generally to devices, systems, and methods to control intraocular pressure during ophthalmic surgery, such as posterior segment surgical procedures including vitrectomy. More particularly, certain aspects of the present disclosure relate to an injection cannula and methods of use thereof, which are useful for injection/extraction of fluids with respect to the eye. Further aspects of the present disclosure relate to an infusion cannula and methods of use thereof, which are useful for infusion/venting of fluids with respect to the eye.

Certain aspects provide a cannula device for a surgical procedure having a proximal segment comprising a first inner diameter (ID), a first proximal end, and a first distal end; and a distal segment comprising a second ID smaller than the first ID, a second proximal end, and a second distal end configured to be disposed inside a hub or a cannula transition of a valved cannula comprising the hub, a shaft, and the cannula transition between the hub and the shaft.

Certain aspects provide a cannula device for a surgical procedure having a proximal segment comprising a first inner diameter (ID), a first proximal end, and a first distal end; an intermediate segment comprising a second ID smaller than the first ID, a second proximal end, and a second distal end; a first transition connecting the proximal segment and the intermediate segment via the first distal end and the second proximal end, the first transition comprising a first fillet and a second fillet; a distal segment comprising a third ID smaller than the second ID, a third proximal end, and a third distal end; and a second transition connecting the intermediate segment and the distal segment via the second distal end and the third proximal end, the second transition comprising a third fillet and a fourth fillet.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure. Figures disclosed herein may not be to scale.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

In the following description, details are set forth by way of example to facilitate an understanding of the disclosed subject matter. It should be apparent to a person of ordinary skill in the art, however, that the disclosed implementations are exemplary and not exhaustive of all possible implementations. Thus, it should be understood that reference to the described examples is not intended to limit the scope of the disclosure. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

Note that, as described herein, a distal end, segment, or portion of a component refers to the end, segment, or portion that is closer to a patient's body during use thereof. On the other hand, a proximal end, segment, or portion of the component refers to the end, segment, or portion that is distanced further away from the patient's body. An intermediate segment or portion of a component refers to the segment or portion that is positioned between the distal segment or portion and the proximal end or portion.

As used herein, the term "about" may refer to a +/−10% variation from the nominal value. It is to be understood that such a variation can be included in any value provided herein.

Embodiments of the present disclosure provide devices, systems, and methods to control intraocular pressure (IOP) and/or administer fluids, such as ocular tamponades, to the ocular space. More particularly, embodiments described herein disclose injection cannulas and methods of use thereof, which are useful for injection and/or extraction of fluids with respect to the eye as described in more detail below. Further aspects of the present disclosure relate to infusion cannulas and methods of use thereof, which are useful for infusion and/or venting of fluids with respect to the eye as described in more detail below. Further, techniques and designs discussed herein may be similarly applicable to other types of fluid cannulas. Note that, as described herein, although the fluid cannulas are coupled to the valved cannula, certain aspects may use a non-valved cannula instead of the valved cannula. Also note that, although described with reference to vitreoretinal procedures, the devices, systems, and methods described herein are also applicable to other types of cannulas or uses and are not solely limited to ophthalmic procedures.

Conventional fluid cannulas include an inner diameter (ID) that may limit fluid flow to a level that is less than what the valved cannula can actually support. For example, a smallest ID of conventional fluid cannulas is smaller than a corresponding smallest ID of a valved cannula through which the fluid is flowed. The smallest ID of the fluid cannula restricts the fluid flow because a resistance (R) to fluid flow is directly proportional to a viscosity (TO) of the fluid and a length (L) of a passage the fluid is flowing through, where the fluid passage is a portion of the fluid cannula with a constant ID. Furthermore, the resistance to fluid flow is inversely proportional to a radius of the fluid passage to the fourth power ($r^4$), where the radius is one-half of the ID of the fluid passage. Thus, the resistance to fluid flow is also inversely proportional to ID of the fluid passage:

$$R \propto \frac{\eta L}{r^4}$$

Therefore, because conventional fluid cannulas include segments having an ID smaller than the smallest ID of a corresponding valved cannula, these segments of the conventional fluid cannulas limit fluid flow to a level that is less than the valved cannula can actually support.

Certain embodiments described herein provide fluid cannulas that may have one or more of the following features, each of which provide a benefit. The fluid cannula may have a distal segment with a larger ID than a smallest ID of a compatible valved cannula. The larger ID reduces the resistance to fluid flow because resistance is inversely proportional to the ID of the fluid passage. The fluid cannula may have a distal segment with a shorter length than conventional fluid cannulas. The shorter length of the segment reduces the resistance to fluid flow thereof because resistance is proportional to the length of the fluid passage. The fluid cannula may have an intermediate segment to transition between a proximal segment and the distal segment. The intermediate segment reduces the resistance to fluid flow because it provides a larger diameter for a portion of the length inside the compatible valved cannula. The fluid cannula may have transitions between the segments having at least two fillets (e.g., rounds, curves, cutouts, radii, splines, or similar curvatures) and/or chamfers (e.g., bevels). The transitions provide a smooth transition between the segments. Thus, the previously described features are configured to reduce overall flow resistance and pressure drop through the fluid cannulas which lowers the pressure needed to maintain a given fluid flow rate or, stated another way, increases the flow rate at a given source pressure, as described in more detail below.

Figure 1A:
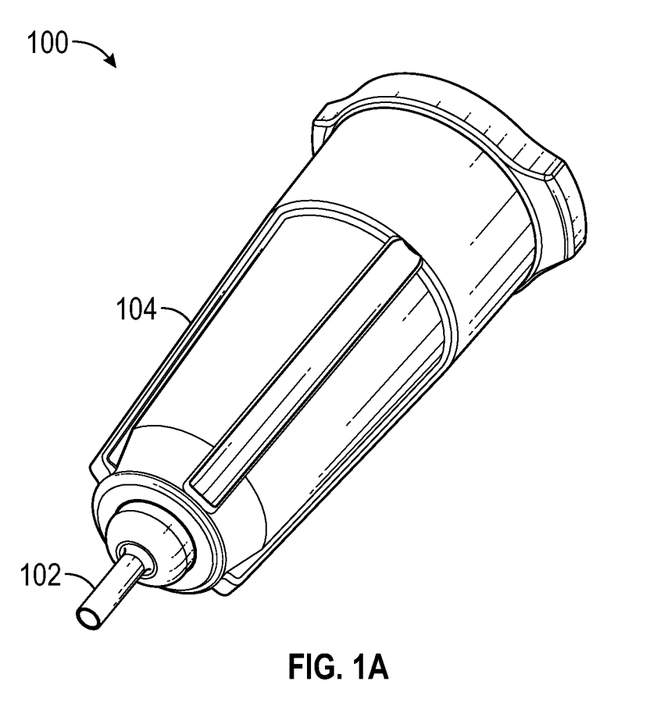
FIGS. 1A-1B depict isometric and cross-sectional side views of an exemplary injection cannula assembly including a viscous fluid control (VFC) cannula, in accordance with certain embodiments of the present disclosure.

FIG. 1A depicts an isometric view of an exemplary injection cannula assembly 100, according to certain embodiments. The injection cannula assembly 100 generally includes a viscous fluid control (VFC) cannula 102 and an adapter 104. The VFC cannula 102 is configured to be inserted into, e.g., a valved cannula (shown in FIGS. 2C-2D), and may be used to inject or extract fluid through the valved cannula into/out of the ocular space of a patient's eye. The adapter 104 connects or adapts the VFC cannula 102 to a receiving device, such as a syringe, which may contain the fluid for injection. A user, such as a surgeon, may inject the fluid from the syringe through the cannula assembly 100 and the valved cannula and into the patient's eye. The user may also use the syringe to extract fluid from the patient's eye. In certain embodiments, the receiving device may be a tubing of a fluid line and may connect to a surgical console at a proximal end thereof opposite the VFC cannula 102. In such embodiments, the surgical console may be configured to control or drive injection or extraction of the fluid at a set pressure and/or flow rate through the fluid line and/or VFC cannula 102.

Figure 1B:
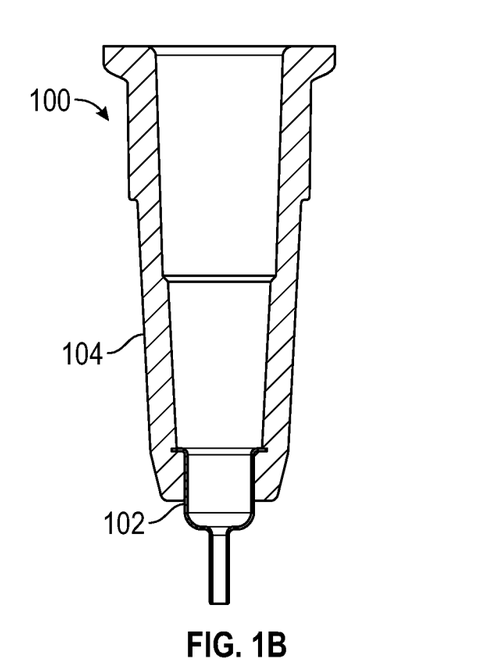

FIG. 1B depicts a cross-sectional side view of the injection cannula assembly 100 with the VFC cannula 102. In particular, FIG. 1B shows an interior profile and interior features of the VFC cannula 102.

As shown, the VFC cannula 102 connects to the adapter 104, and may be made of similar or different materials thereto. In certain embodiments, the VFC cannula 102 comprises a metallic material, such as stainless steel or carbon steel. In certain embodiments, the VFC cannula 102 comprises a protective coating formed thereon, such as nickel plating, to resist corrosion and/or microbial growth. In certain embodiments, adapter 104 comprises a thermoplastic elastomer or a rigid polymer such as polycarbonate, polyethylene, polypropylene, or the like.

The VFC cannula 102 and adapter 104 may be manufactured using similar or different manufacturing processes. In certain embodiments, the VFC cannula 102 may be manufactured using a deep draw process or a machining process. In certain embodiments, the adapter 104 may be manufactured using an injection mold process. In certain embodiments, the adapter 104 may be manufactured around the VFC cannula 102 via an insert molding or injection overmolding process. In certain embodiments, either one or both of the VFC cannula 102 and the adapter 104 may be manufactured using three-dimensional (3D) printing. In certain embodiments where the VFC cannula 102 and the adapter 104 are separately manufactured, the VFC cannula 102 and the adapter 104 may connect mechanically, such as through slots and tabs, or attach using an adhesive or thermal bonding.

Figure 2A:
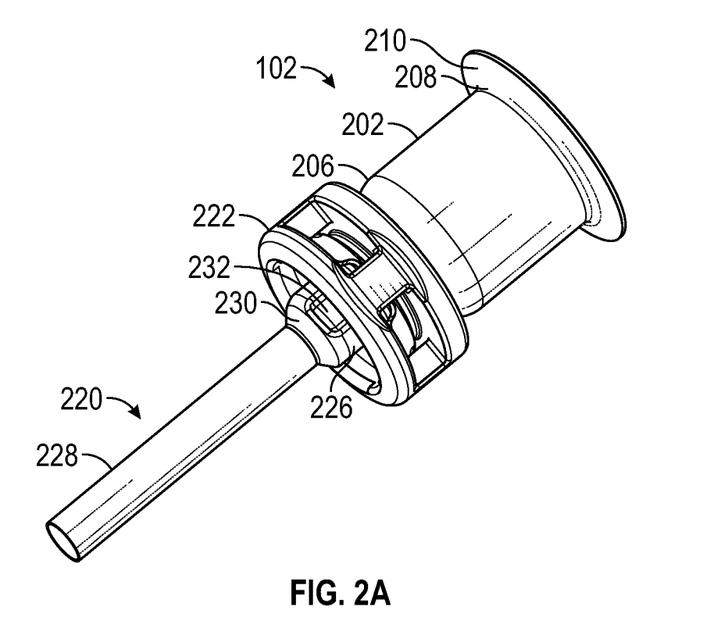
FIGS. 2A-2B depict isometric and cross-sectional side views of the VFC cannula of FIGS. 1A and 1B coupled to a valved cannula, in accordance with certain embodiments of the present disclosure.
Figure 2B:
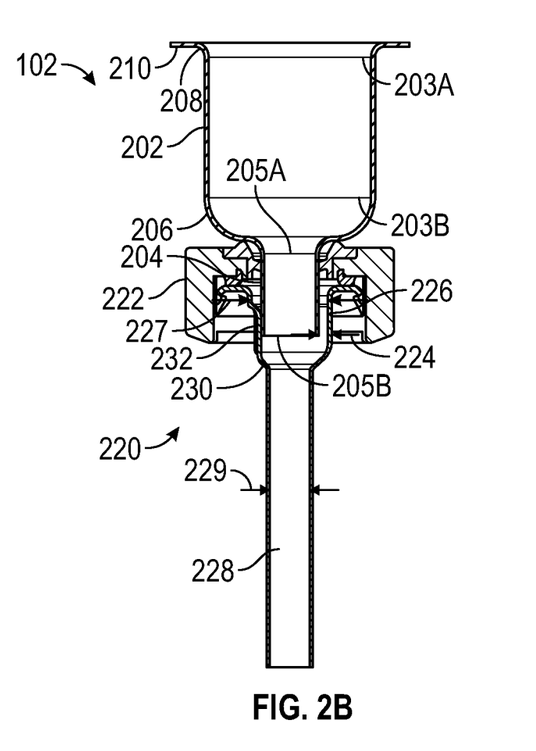

FIGS. 2A and 2B depict isometric and cross-sectional side views of the VFC cannula 102 coupled to a valved cannula 220, respectively. In particular, FIGS. 2A and 2B show an exterior profile and exterior features of the VFC cannula 102 that is coupled to the valved cannula 220. The VFC cannula 102 is configured to be inserted into the valved cannula 220 to inject, vent, or extract fluid through the valved cannula and into or out of the ocular space of a patient's eye.

As shown, the VFC cannula 102 includes a proximal segment 202 and a distal segment 204. The proximal segment 202 includes a first proximal end 203A and a first distal end 203B. The distal segment 204 includes a second proximal end 205A and a second distal end 205B. A first transition 206 connects the proximal segment 202 and the distal segment 204 via the first distal end 203B and the second proximal end 205A. In certain embodiments, a second transition 208 connects the proximal segment 202 and a top rim 210 at the first proximal end 203A. The second transition 208 and/or the top rim 210 may be molded into or adhere to an adapter (e.g., the adapter 104 in FIG. 1B). In certain embodiments, the VFC cannula 102 does not have a top rim, and the proximal segment 202 is the most proximal portion thereof.

The valved cannula 220 generally includes an overcap 222, a hub 226, and a hollow tube or shaft 228. The hub 226 and the shaft 228 are connected by a cannula transition 230. An inner diameter (ID) (e.g., an ID 227 in FIG. 2B) of the hub 226 is larger than an ID (e.g., an ID 229 in FIG. 2B) of the shaft 228. The valved cannula 220 further includes an indentation 232, which may be part of the hub 226 and/or the cannula transition 230.

As shown in FIG. 2B, the second distal end 205B of the distal segment 204 of VFC cannula 102 is disposed inside the hub 226 when the VFC cannula 102 is coupled to the valved cannula 220. In certain embodiments, to couple the VFC cannula 102 to the valved cannula 220, at least a portion of the VFC cannula 102 frictionally engages with an inner feature of the valved cannula 220 when the VFC cannula 102 is inserted into the valved cannula 220. For example, at least a portion of the distal segment 204 frictionally engages with the inner feature of valved cannula 220, where the inner feature includes the indentation 232 and/or an inner wall of valved cannula 220.

In certain embodiments, indentation 232 is dimensioned to provide enough resistance between the VFC cannula 102 and the valved cannula 220 to keep the VFC cannula 102 in place during a procedure. In certain embodiments, the resistance between the indentation 232 and the VFC cannula 102 is less than needed to pull the valved cannula 220 out of the eye when withdrawing the VFC cannula 102 from the valved cannula 220. For example, the valved cannula 220 is not pulled out of the eye when the VFC cannula 102 is pulled out of the valved cannula 220 while the valved cannula 220 is in the eye. In certain embodiments, the resistance between the VFC cannula 102 and the valved cannula 220 is such that the VFC cannula 102 cannot be decoupled from the valved cannula 220 without removing valved cannula 220 from the eye. In certain embodiments, the resistance is formed between other areas or sections of the VFC cannula 102 and the valved cannula 220. For example, in some embodiments, the exterior of the distal segment 204 frictionally engages with the interior surface of the hub 226 and/or cannula transition 230.

As further shown in FIG. 2B, the hub 226 of the valved cannula 220 radially surrounds and couples to the distal segment 204 of the VFC cannula 102 when the VFC cannula 102 is inserted into the valved cannula 220. In certain embodiments, when inserted into the valved cannula 220, the distal segment 204 is disposed only inside (i.e., radially inward of) the hub 226, or disposed only inside the hub 226 and the cannula transition 230, and the distal segment 204 does not extend into the shaft 228. Because the distal segment 204 does not extend into the shaft 228, the dimensions of the distal segment 204 are not restricted by the dimensions of the shaft 228, and in certain embodiments, a smallest ID (e.g., a second ID 242 in FIG. 2D) of the distal segment 204 is greater than the ID 229 of the shaft 228 of the valved cannula 220. As previously described, the valved cannula 220 may be a 23 gauge valved cannula, a 25 gauge valved cannula, a 27 gauge valved cannula, and the like. The relatively greater ID (e.g., the second ID 242 in FIG. 2D) of the distal segment 204 of the VFC cannula 102 compared to the ID 229 of the shaft 228 is configured to reduce overall flow resistance and pressure drop through the VFC cannula 102 because the valved cannula 220 limits fluid flow to a level that is less than what the VFC cannula can actually support.

The shortened distal segment 204 further enables a universal fit for the VFC cannula 102 with valved cannulas of different gauges, since the distal segment 204 is not required to conform to the different IDs (e.g., the ID 229) of the shafts (e.g., the shaft 228) thereof. For example, the VFC cannula may universally couple to a 23 gauge valved cannula, 25 gauge valved cannula, 27 gauge valved cannula, and the like. Accordingly, the versatility of the VFC cannula 102 beneficially reduces the number of different parts needed for a surgical procedure.

In certain embodiments, the VFC cannula 102 may also provide pressure relief and/or tactile feedback for a user when injecting a fluid into a patient's eye. For example, in certain embodiments, a gap 224 is formed between the distal segment 204 and the hub 226 when the VFC cannula 102 is inserted into the valved cannula 220. In such embodiments, the gap 224 between the distal segment 204 and the valved cannula 220 allows injected fluid to backflow out of the valved cannula 220 and through the overcap 222 because the VFC cannula 102 does not completely seal against the valved cannula 220. The backflow may occur when the pressure in the eye is higher than the pressure exerted by the user and allows the physician to better feel a resistance when injecting the fluid into the eye.

Note that, in certain embodiments, an exterior of the distal segment 204 may connect to, couple to, or mate with an interior of the hub 226 and/or the cannula transition 230 such that no gap is formed therebetween.

In certain embodiments, the VFC cannula 102 includes a retention feature to frictionally engage with the inner feature of the valved cannula 220. For example, the distal segment 204 may have an indentation or other feature configured to mate with, closely fit, and/or conform to the indentation 232.

Because of the relatively large ID and short length of the distal segment 204, a lower source pressure may be used to maintain a given flow rate with the VFC cannula 102 disclosed herein. In certain embodiments, the source pressure is reduced proportional to the decrease in flow resistance. In certain embodiments, the flow rate is increased at a given source pressure with injection cannula embodiments disclosed herein. In certain embodiments, the increase in the flow rate is generally about 5-30% or more. In certain embodiments, such as at 80 psi source pressure, the increase in the flow rate is about 15-30% or greater as compared to conventional 25 gauge injection cannula designs. In certain embodiments, such as at 30 psi source pressure, the increase in the flow rate is about 5-20% or greater compared to conventional 25 gauge injection cannula designs.

Figure 2C:
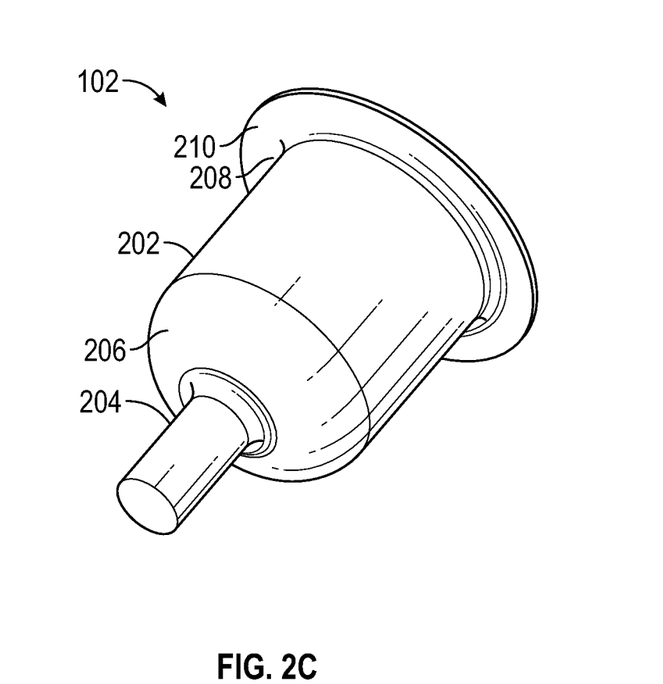
FIGS. 2C-2D depict isometric and cross-sectional side views of the VFC cannula of FIGS. 1A and 1B, in accordance with certain embodiments of the present disclosure.
Figure 2D:
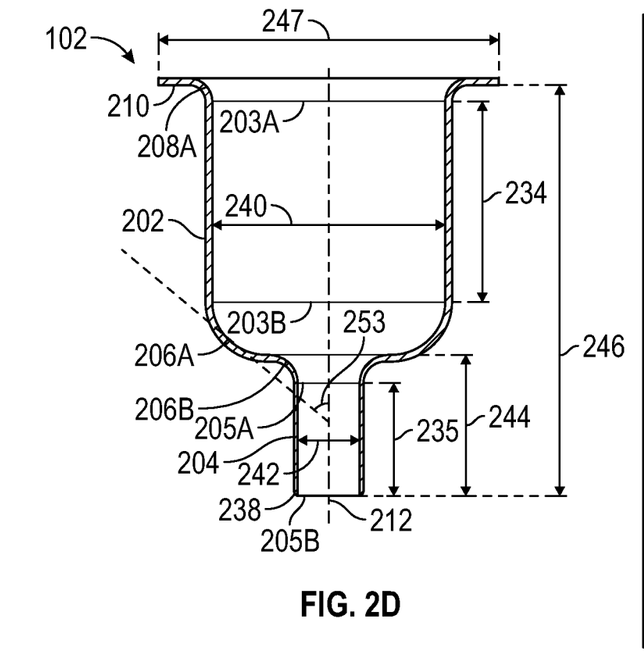

FIGS. 2C and 2D depict isometric and cross-sectional side views of the VFC cannula 102, respectively. In particular, FIGS. 2C and 2D show an exterior profile and exterior features of the VFC cannula 102, and FIG. 2D includes several example dimensions provided in inches unless otherwise noted. Note that the labeled dimensions are only exemplary, and that other dimensions for the features may be utilized, including in different ratios.

As shown, the proximal segment 202 has a first ID 240 and the distal segment 204 has a second ID 242. In certain embodiments, the distal segment 204 has inner dimensions, e.g., the second ID 242, of between about 0.020 and about 0.030 inches, such as between about 0.020 inches and about 0.028 inches, such as about 0.023 inches. In certain embodiments, the inner dimensions of the distal segment 204 are greater than 0.030 inches, such as when an exterior of the distal segment 204 conforms to the inside of the valved cannula hub (e.g., the hub 226 in FIG. 2B) and/or the cannula transition (e.g., the cannula transition 230 in FIG. 2B), or when the distal segment 204 has an indentation.

In certain embodiments, the VFC cannula 102 has an internal shaft length 244 (e.g., including distal segment 204 and a fillet 206B) of between about 0.050 inches and about 0.120 inches, such as about 0.0507 inches. In certain embodiments, the VFC cannula 102 has a total length 246 of between about 0.150 and about 0.250 inches, such as between about 0.156 and about 0.203 inches, such as about 0.156 inches. Thus, in some embodiments, a ratio of the internal shaft length 244 to total length 246 for the VFC cannula may be between about 0.2 and about 0.4, such as about (0.0507 inches/0.156 inches=0.325). In certain embodiments, the VFC cannula 102 has a total width 247, which may be a diameter of between about 0.110 inches and about 0.140 inches, such as about 0.126 inches. Generally, the segments 202 and 204 and the transitions 206 and 208 share a common central axis 212 disposed through a center of the VFC cannula 102. In certain embodiments, the proximal segment 202 measures a first length 234 along the central axis 212 and the distal segment 204 measures a second length 235 along the central axis 212. The second length 235 may be more than, less than, or equal to the first length 234. Note that although described with segments 202 and 204 and transitions 206 and 208, the VFC cannula 102 may be formed from a single, unitary body and the segments 202 and 204 and the transitions 206 and 208 may refer to portions of the unitary body. Note that although features are described herein with particular dimensions or ranges of dimensions, other dimensions and/or IDs are further contemplated.

In certain embodiments, the first transition 206 includes a first fillet 206A and a second fillet 206B, and the second transition 208 includes a third fillet 208A. In certain embodiments, the first fillet 206A is concave and the second fillet 206B is convex. In certain embodiments, the third fillet 208A is concave, while in further embodiments, the third fillet 208A is convex.

As shown in FIG. 2D, the fillets 206A, 206B and 208A are formed on inner walls of the transitions 206 and 208. In certain embodiments, fillets are formed on inner and/or outer walls of transitions 206 and 208. In certain embodiments, inner and/or outer walls of the segments 202 and 204 are parallel or tapered relative to the central axis 212. In some embodiments, the wall thicknesses of the segments 202 and 204 and the first and second transitions 206 and 208 are constant. In some embodiments, the wall thicknesses may be variable or may vary by feature (e.g., the first transition 206, the distal segment 204).

In certain embodiments, the first transition 206 includes a first chamfer or bevel (e.g., similar to first chamfer 406C in FIG. 4D) rather than a fillet (e.g., fillets 206A and 206B). In certain embodiments, the second distal end 205B includes a fourth fillet 238, which may be convex, and/or a second chamfer.

Fillets described herein, including fillets 206A and 206B, may have one or more positional angles (e.g., positional angle 253) to reference the location of a midpoint of the fillet relative to the central axis 212. The positional angles may measure between the central axis 212 and a tangential line of the midpoint of the fillet. For example, the positional angle 253 may be between 1 and 85 degrees. For example, the positional angle 253 may be between 10 and 60 degrees. For example, the positional angle 253 may be between 20 and 40 degrees. For example, the positional angle 253 may be about 26 degrees. In certain embodiments, the fillet may be on an inner surface of the transition (e.g., the first transition 206). In further embodiments, the fillet may be on an outer surface of the transition.

In certain embodiments, a continuous flow path is formed between the first proximal end 203A and the second distal end 205B of the VFC cannula 102. Accordingly, curvatures of the transitions 206 and 208 may allow a fluid to smoothly flow through the VFC cannula 102 by reducing fluid friction losses, thereby beneficially improving fluidic performance. In certain embodiments, the inner walls of the segments 202 and 204 and the transitions 206 and 208 connect seamlessly to form a smooth inner profile such that there are no disjointed transitions, interruptions, or indications of disparity between the segments 202 and 204 and the transitions 206 and 208.

Figure 2E:
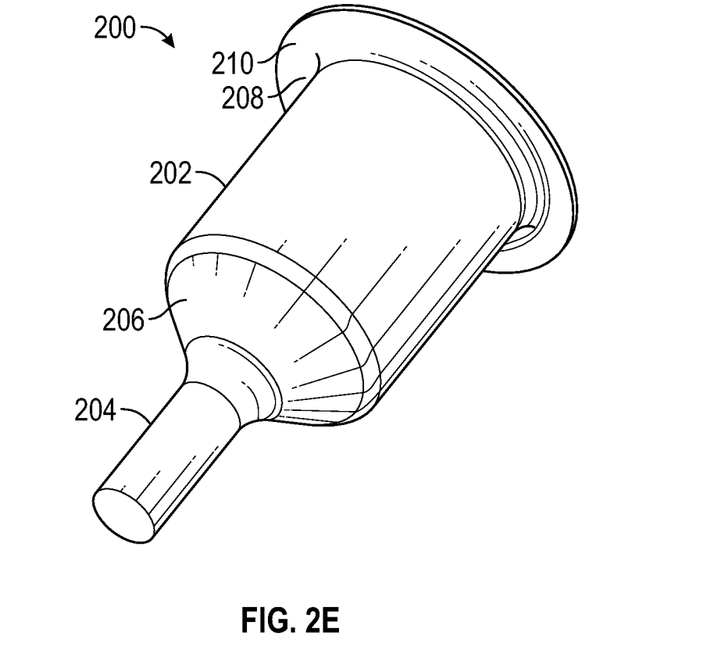
FIGS. 2E-2F depict isometric and cross-sectional side views of an alternative VFC cannula to FIGS. 1A and 1B, in accordance with certain embodiments of the present disclosure.
Figure 2F:
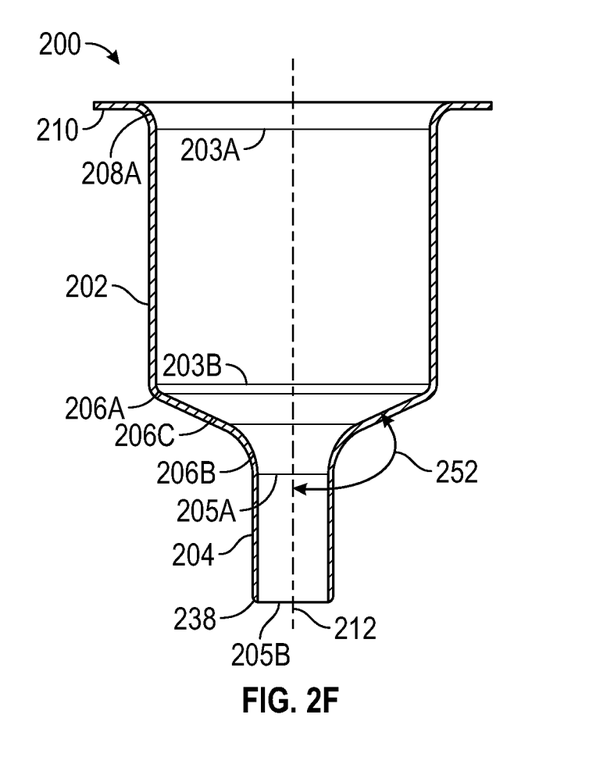

FIGS. 2E and 2F depict isometric and cross-sectional side views of another VFC cannula, shown as VFC cannula 200, respectively. In particular, FIGS. 2E and 2F show an exterior profile and exterior features of the VFC cannula 200. The VFC cannula 200 is substantially similar to VFC cannula 102, and uses similar reference numerals where appropriate.

However, unlike the VFC cannula 102, the first transition 206 of VFC cannula 200 includes a first chamfer or bevel 206C disposed between the fillets 206A and 206B. In certain embodiments, a transition angle θ (e.g., a first transition angle 252 in FIG. 2F) measures between the first chamfer 206C and an axis of one of the segments 202 or 204, which may not be collinear with the central axis 212. In certain embodiments, the transition angle θ measures between the first chamfer 206C and the central axis 212. In certain embodiments, the transition angle θ is about 120 degrees, but in further embodiments may be about 90 degrees and up to and including about 165 degrees. In further embodiments, the transition angle θ is more than 90 degrees.

The morphology of the first transition 206 may improve the flow of fluid through the VFC cannula 200. As shown, the first transition 206 includes the first chamfer 206C which forms a funnel-shaped feature in the VFC cannula 200 having a gradual reduction in ID between the proximal segment 202 and the distal segment 204. The chamfer facilitates prevention of excessive pressure loss when compared to the transition of conventional VFC cannulas by providing a gradual, linearly decreasing reduction in the cross section for the fluid.

Figure 3A:
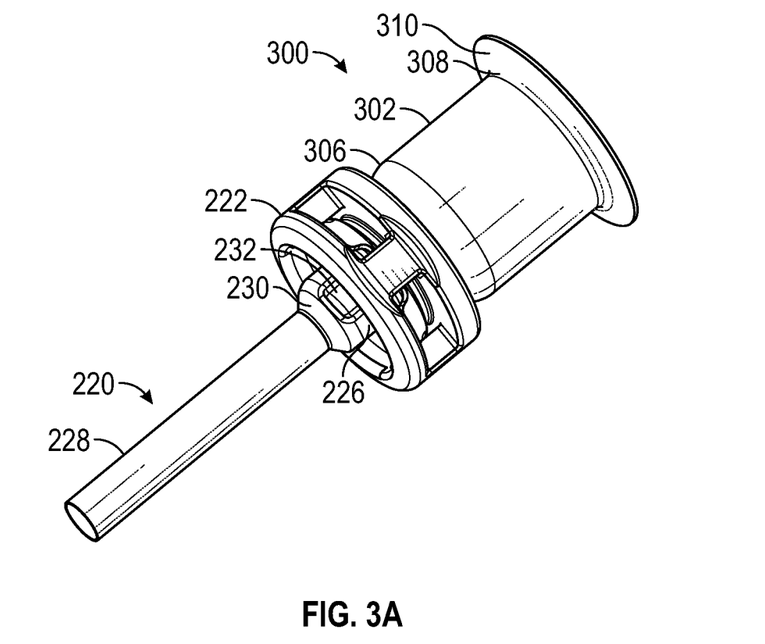
FIGS. 3A-3B depict isometric and cross-sectional side views of an alternative VFC cannula coupled to a valved cannula, in accordance with certain embodiments of the present disclosure.
Figure 3B:
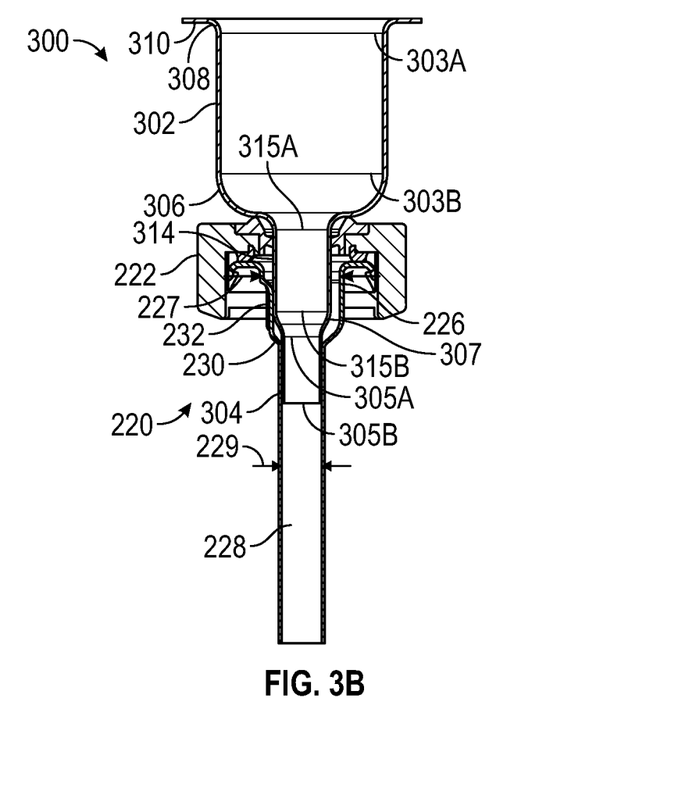

FIGS. 3A and 3B depict isometric and cross-sectional side views of an alternative VFC cannula 300 coupled to the valved cannula 220, respectively. In particular, FIGS. 3A-3B show an exterior profile and exterior features of the VFC cannula 300 and the valved cannula 120.

As shown, the VFC cannula 300 includes a proximal segment 302, an intermediate segment 314, and a distal segment 304. The proximal segment 302 includes a first proximal end 303A and a first distal end 303B; the intermediate segment 314 includes a second proximal end 315A and second distal end 315B; and, the distal segment 304 includes a third proximal end 305A and third distal end 305B. A first transition 306 connects the proximal segment 302 and the intermediate segment 314 at the first distal end 303B and the second proximal end 315A. A second transition 307 connects the intermediate segment 314 and the distal segment 304 at the second distal end 315B and the third proximal end 305A. In certain embodiments, a third transition 308 connects the proximal segment 302 and a top rim 310 at the first proximal end 303A. The third transition 308 and/or the top rim 310 may be molded into or adhere to an adapter (e.g., the adapter 104 in FIG. 1B). In certain embodiments, the VFC cannula 300 does not include a top rim.

Similar to the VFC cannula 102, the VFC cannula 300 is configured to be inserted into the valved cannula 220 to inject, vent, or extract fluid through the valved cannula and into the ocular space of a patient's eye. In certain embodiments, at least a portion of the VFC cannula 300 frictionally engages with an inner feature of valved cannula 220 when the VFC cannula 300 is inserted therein. For example, at least a portion of intermediate segment 314 frictionally engages with the inner feature of valved cannula 220, and/or at least a portion of the distal segment 304 frictionally engages with an inside of the shaft 228, resulting in a "tube in tube" configuration between the distal segment 304 and the shaft 228. The tube in tube configuration results in a stable fluid flow and operating pressure when using the VFC cannula 300. In certain embodiments, the distal segment 304 of the VFC cannula 300 is sized to closely fit a specific gauge size of the valved cannula 220. For example, the distal segment 304 has an outer diameter configured to closely fit within the shaft 228 of a 23 gauge valved cannula, a 25 gauge valved cannula, a 27 gauge valved cannula, or the like.

A different injection cannula may include a unitary body formed of two cylinders of uniform diameters: a wide proximal cylinder and a narrow distal cylinder. The narrow distal cylinder has an ID smaller than the ID of the shaft 228 of the valved cannula 220. The cylinders are connected by a transition consisting of two fillets such that the flow path experiences a sharp reduction in an ID when transitioning between the wide proximal cylinder and the narrow distal cylinder. The sudden reduction in ID increases the flow resistance therethrough. The transition is positioned at the overcap 222 of the valved cannula when the different injection cannula is coupled to the valved cannula 220. When coupled, the narrow distal cylinder extends from the overcap 222, through the hub 226, and into the shaft 228 of the valved cannula 220. Thus, the different injection cannula is the limiting factor for fluid flow because it requires fluid flow through the smallest ID at a length extending from the overcap 222 and into the shaft 228.

In comparison, the VFC cannula 300 is segmented into at least three segments 302, 314, and 304 with three different IDs. Thus, different segments (e.g., 314 and 304) may be passed through different portions (e.g., the hub 226 or the shaft 228) of the valved cannula 220 when the VFC cannula 300 is coupled thereto. Accordingly, the intermediate segment 314 may be disposed within the hub 226 and may have an increased ID relative to the distal segment 304 within the shaft 228, and the distal segment 304, having the smallest ID, may have a reduced length through the shaft 228. The reduced length of the distal segment 304 having the smallest ID, in addition to the increased ID within the hub 226, beneficially reduces fluid flow resistance of the VFC cannula 300. Thus, in certain embodiments, a lower source pressure may be used to maintain a given flow rate with the VFC cannula embodiments disclosed herein, and source pressure may be reduced proportional to the decrease in flow resistance.

In certain embodiments, the distal segment 304 is shorter because some of the length of the VFC cannula 300 extending into the valved cannula 220 is taken up by the intermediate segment 314, which has a larger ID than the distal segment 304. As shown in FIG. 3B, the length of the VFC cannula 300 extending into the valved cannula 220 may be the same as or shorter than conventional fluid cannula designs. The shorter distal segment 304 may generally increase the flow rate of the VFC cannula 300 as compared to conventional cannula designs. For example, the shorter distal segment 304 may increase the flow rate about 5-30% or greater compared to conventional fluid cannula designs, such as about 8-28% when flowing 1000 cSt (centistokes) silicone oil at 60 psi (pound-force per square inch) into the eye. The flow rate is generally affected by the input pressure and viscosity of fluids being flowed through the VFC cannula 300. The flow rate is further affected by the ID of the segments, because narrowing the cross section increases the pressure loss, leading to a decreased flow rate. Shortening the distal segment 304 reduces the distance the fluid flows through a smallest ID (e.g., the third ID) and prevents an excessive pressure loss by providing a longer, wider cross section for the fluid.

Similar to the VFC cannula 102, the VFC cannula 300 may also include a retention feature to frictionally engage with the inner feature of the valved cannula 220 in certain embodiments. For example, the intermediate segment 314 may have an indentation configured to mate with, closely fit, and/or conform to the indentation 232.

Figure 3C:
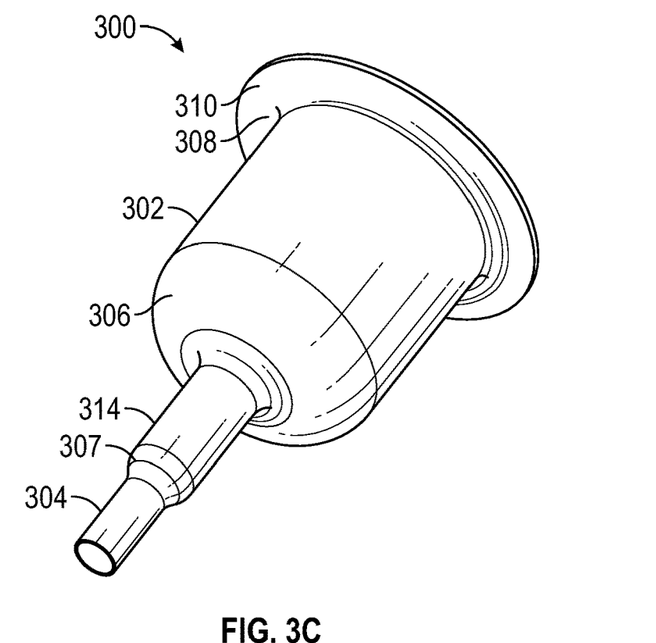
FIGS. 3C-3D depict isometric and cross-sectional side views of the alternative VFC cannula of FIG. 3A, in accordance with certain embodiments of the present disclosure.
Figure 3D:
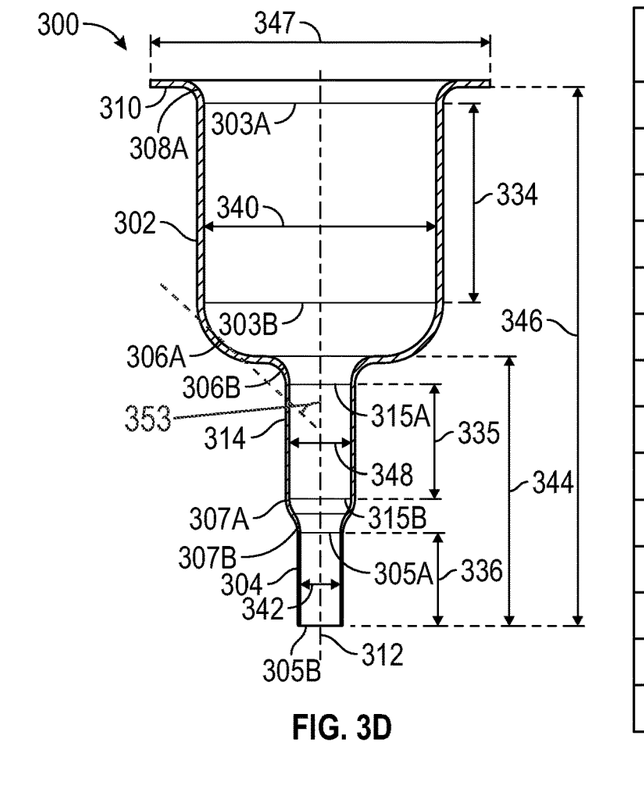

FIGS. 3C and 3D depict isometric and cross-sectional side views of the VFC cannula 300, respectively. In particular, FIG. 3D shows an interior profile and interior features of the VFC cannula 300, and FIG. 3D includes several example dimensions provided in inches unless otherwise noted.

As shown, the proximal segment 302 has a first ID 340, the intermediate segment 314 has a second ID 348, and the distal segment 304 has a third ID 342. In certain embodiments, the intermediate segment 314 has inner dimensions, e.g., the second ID 348, of between about 0.020 and about 0.030 inches, such as between about 0.023 and about 0.028 inches, such as about 0.023 inches. In certain embodiments, the inner dimensions of the intermediate segment 314 are greater than 0.030 inches, such as when an exterior of the intermediate segment 314 conforms to the inside of the valved cannula hub (e.g., the hub 226 in FIG. 3B) and/or the cannula transition (e.g., the cannula transition 230 in FIG. 3B), or when the distal segment 304 has an indentation.

In certain embodiments, the VFC cannula 300 has an internal shaft length 344 (e.g., distal segment 304, transition 307, intermediate segment 314, and fillet 306B) that may be longer than the internal shaft length 244 in FIG. 2D (e.g., internal shaft length 344 may be between about 0.07 inches and about 0.126 inches, such as 0.098 inches), and a total length 346 between about 0.150 and about 0.250 inches, such as about 0.203 inches. Thus, in some embodiments, a ratio of the internal shaft length 344 to total length 346 for the VFC cannula may be between about 0.35 and about 0.55, such as about (0.098 inches/0.203 inches=0.483). In certain embodiments, the VFC cannula 300 has a total width 347, which may be a diameter of between about 0.110 inches and about 0.140 inches, such as about 0.126 inches. Similar to the VFC cannula 102, the segments 302, 304, and 314 and the transitions 306, 307, and 308 share a common central axis 312 disposed through a center of the VFC cannula 300, which is formed from a single, unitary body. In certain embodiments, the proximal segment 302 measures a first length 334, the intermediate segment 314 measures a second length 335, and the distal segment 304 measures a third length 336, each measured along the central axis 312. The third length 336 may be more than, less than, or equal to the second length 335. In further embodiments, the third length 336 is zero, and the VFC cannula 300 has a total length 346 extending between top rim 310 and a distal end of transition 307 (e.g., the VFC cannula 300 does not include the distal segment 304). Note that although features are described herein with particular dimensions or ranges of dimensions, other dimensions and/or IDs are further contemplated.

In certain embodiments, the first transition 306 includes a first fillet 306A and a second fillet 306B, the second transition 307 includes a third fillet 307A and a fourth fillet 307B, and third transition 308 includes a fifth fillet 308A. In certain embodiments, the first fillet 306A is concave and the second fillet 306B is convex. In certain embodiments, the third fillet 307A is concave and the fourth fillet 307B is convex. In certain embodiments, the fifth fillet 308A is concave, while in other embodiments, the fifth fillet 308A is convex. In certain embodiments, the third distal end 305B may include a sixth fillet and/or a second chamfer (e.g., the fourth fillet 238 in FIG. 2D) or bevel similar to as described in FIG. 2D. The sixth fillet and/or the second chamfer may beneficially facilitate the insertion of the VFC cannula 102 into the valved cannula 220 by gradually increasing the outer diameter of the third distal end 305B.

As shown in FIG. 3D, the fillets 306A, 306B, 307A, 307B and 308A are formed on inner walls of the transitions 306, 307, and 308. In certain embodiments, the fillets are formed on inner and/or outer walls of the transitions 306, 307, and 308. In certain embodiments, the walls of the segments 302, 304, and 314 are configured substantially similar to the walls of the VFC cannula 102 previously described in FIG. 2D. For example, fillets 306A and 306B, may have one or more positional angles (e.g., positional angle 353) to reference the location of a midpoint of the fillet relative to the central axis 312. The positional angles may measure between the central axis 312 and a tangential line of the midpoint of the fillet. For example, the positional angle 353 may be between 1 and 85 degrees. For example, the positional angle 353 may be between 10 and 60 degrees. For example, the positional angle 353 may be between 20 and 40 degrees. For example, the positional angle 353 may be about 26 degrees.

In certain embodiments, a continuous flow path is formed between the first proximal end 303A and the third distal end 305B of the VFC cannula 300, and curvatures of the transitions enable a fluid to smoothly flow through the VFC cannula 300 by reducing fluid friction losses, thereby beneficially improving fluidic performance.

Figure 4A:
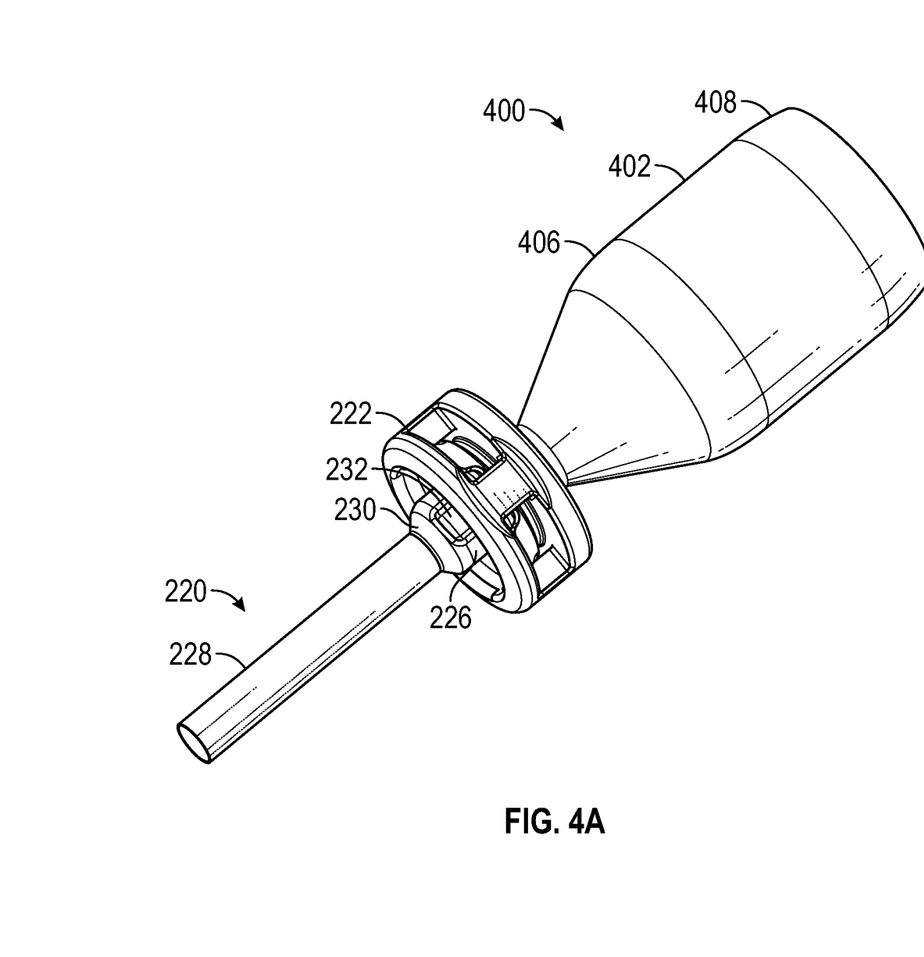
FIGS. 4A-4B depict isometric and cross-sectional side views of an exemplary infusion cannula coupled to a valved cannula, in accordance with certain embodiments of the present disclosure.
Figure 4B:
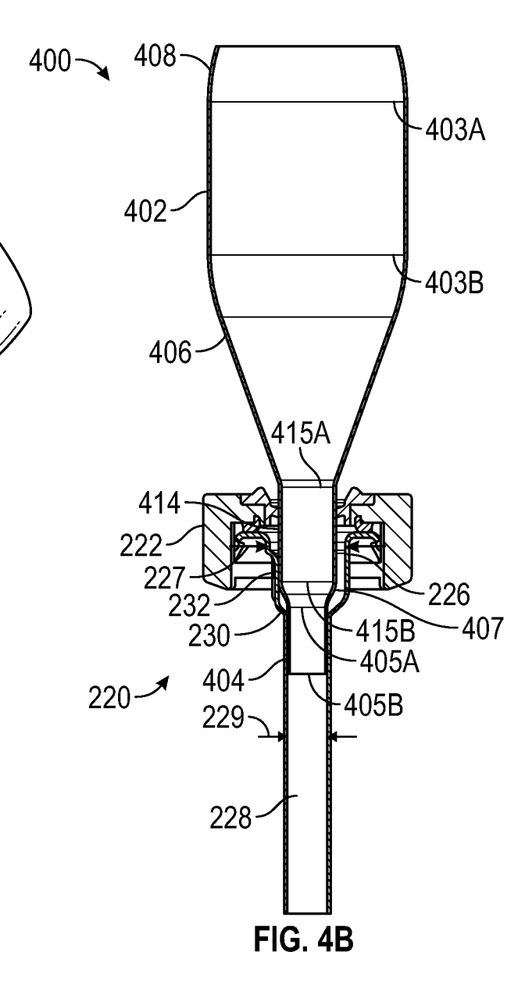

FIGS. 4A and 4B depict isometric and cross-sectional side views of an exemplary infusion cannula 400 coupled to the valved cannula 220. In particular, FIGS. 4A and 4B show an exterior profile and exterior features of the infusion cannula 400 and the valved cannula 220. The infusion cannula 400 is configured to be inserted into the valved cannula 220 to infuse or vent fluid through the valved cannula and into the ocular space of a patient's eye.

Similar to the VFC cannula 300, the infusion cannula 400 includes a proximal segment 402, an intermediate segment 414, and a distal segment 404. The proximal segment 402 includes a first proximal end 403A and a first distal end 403B; the intermediate segment 414 includes a second proximal end 415A and second distal end 415B; and, the distal segment 404 includes a third proximal end 405A and third distal end 405B. A first transition 406 connects the proximal segment 402 and the intermediate segment 414 at the first distal end 403B and the second proximal end 415A. A second transition 407 connects the intermediate segment 414 and the distal segment 404 at the second distal end 415B and the third proximal end 405A. A third transition 408 is configured to connect the proximal segment 402 and a tubing of an infusion line at the first proximal end 403A.

Similar to VFC cannula 300, in certain embodiments, at least a portion of the infusion cannula 400 frictionally engages with an inner feature of valved cannula 220 when the infusion cannula 400 is inserted therein. For example, at least a portion of intermediate segment 414 frictionally engages with the inner feature of valved cannula 220, and/or at least a portion of the distal segment 404 frictionally engages with an inside of the shaft 228, resulting in a "tube in tube" configuration, where the distal segment 404 of the infusion cannula 400 may be sized to closely fit a specific gauge size of valved cannulas.

A different infusion cannula has a unitary body formed of three cylinders of uniform diameters: a wide proximal cylinder, a middle intermediate cylinder, and a narrow distal cylinder. The middle intermediate and wide proximal cylinders are connected by a transition consisting of two fillets such that the flow path experiences a reduction in an ID when transitioning between the middle intermediate cylinder and the narrow distal cylinder. The sudden reduction in ID increases the flow resistance. The transition is positioned at the overcap 222 of the valved cannula when the different infusion cannula is coupled to the valved cannula 220. Additionally, the narrow distal cylinder has an ID smaller than the ID of the shaft 228 of the valved cannula 220. When coupled to a valved cannula, the narrow distal cylinder extends into the shaft 228 of the valved cannula. Thus, the transition between the wide proximal segment and the middle intermediate segment and the extended distal segment of the different infusion cannula are the limiting factors for fluid flow because they require fluid flow through the smallest ID at a length extending from the overcap 222 and into the shaft 228.

In comparison, the infusion cannula 400 is segmented into at least three segments 402, 414, and 404 with three different IDs. Thus, different segments (e.g., 414 and 404) may be passed through different portions (e.g., the hub 226 or the shaft 228) of the valved cannula 220 when the infusion cannula 400 is coupled thereto. Accordingly, the intermediate segment 414 within the hub 226 may have an increased ID relative to the distal segment 404 within the shaft 228, and the distal segment 404, having the smallest ID, may have a reduced length through the shaft 228.

In FIG. 4B, the distal segment 404 is shorter because the extended distal segment of a conventional infusion cannula is the limiting factor for fluid flow. The shorter distal segment 404 reduces the distance the fluid flows through the smallest ID (e.g., the third ID) and prevents an excessive pressure loss by providing a longer, wider cross section of the shaft 228 for the fluid to flow. Thus, in certain embodiments, a lower source pressure may be used to maintain a given flow rate with the infusion cannula embodiments disclosed herein, and source pressure may be reduced proportional to the decrease in flow resistance.

Additionally, the morphology of the first transition 406 may improve the flow of fluid through the infusion cannula 400. In certain embodiments, the first transition 406 includes a chamfer (e.g., a first chamfer 406C in FIG. 4D) which forms a funnel-shaped feature in the infusion cannula 400 having a gradual reduction in ID between the proximal segment 402 and the intermediate segment 414. The chamfer facilitates prevention of excessive pressure loss when compared to the transition of the conventional infusion cannula by providing a gradual, linearly decreasing reduction in the cross section for the fluid.

The shorter distal segment 304 and the addition of the chamfer to the first transition 406 may generally increase the flow rate in the infusion cannula 400 and proportionally decrease the pressure drop therein, as compared to conventional infusion or injection cannula designs. For example, in certain embodiments, the flow rate is increased by about 5% to about 30% or greater as compared to conventional cannula designs, and the pressure drop is decreased proportionally, e.g., by about 20% to about 35% or greater. As described above, the flow rate and pressure drop are affected by the ID of the segments, as well as the source pressure and fluid viscosity.

In certain embodiments, the infusion cannula 400 includes a retention feature to frictionally engage with the inner feature of the valved cannula 420. For example, the intermediate segment 414 may have an indentation configured to mate with, closely fit, and/or conform to the indentation 232.

Figure 4C:
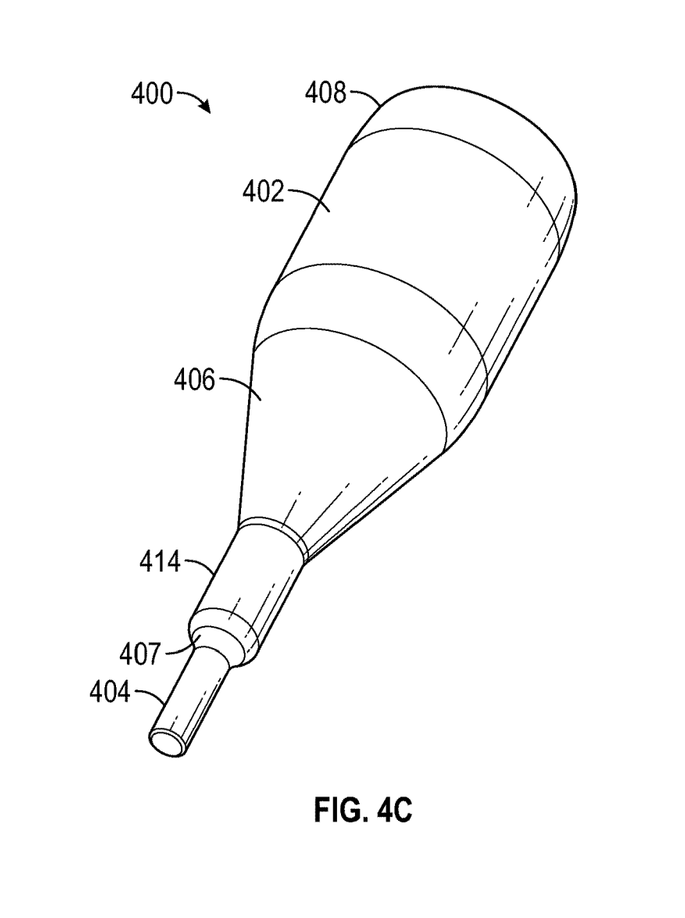
FIGS. 4C-4D depict isometric and cross-sectional side views of the exemplary infusion cannula of FIG. 4A, in accordance with certain embodiments of the present disclosure.
Figure 4D:
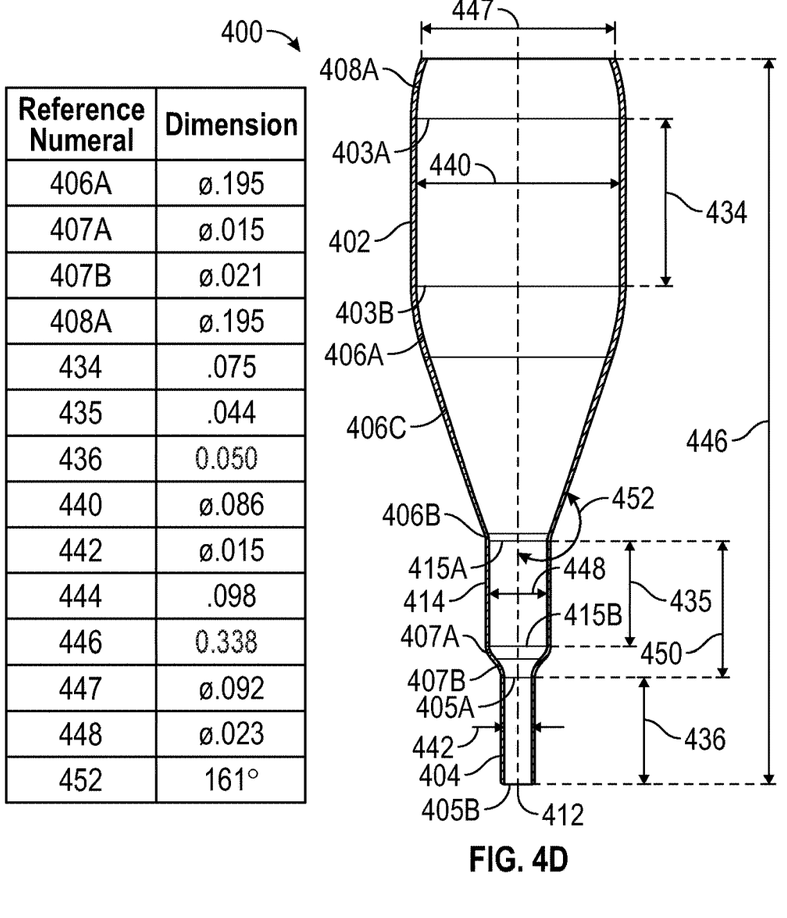

FIGS. 4C and 4D depict isometric and cross-sectional side views of the infusion cannula 400, respectively. In particular, FIG. 4C shows an interior profile and interior features of the infusion cannula 400, and FIG. 4D includes several example dimensions provided in inches unless otherwise noted.

As shown, the proximal segment 402 has a first ID 440, the intermediate segment 414 has a second ID 448, and the distal segment 404 has a third ID 442. In certain embodiments, the intermediate segment 414 has inner dimensions, e.g., the second ID 448, of between about 0.020 and about 0.030 inches, such as between about 0.023 and about 0.028 inches, such as about 0.028 inches. In certain embodiments, the inner dimensions of the intermediate segment 414 are greater than 0.030 inches, such as when an exterior of the intermediate segment 414 conforms to the inside of the valved cannula hub (e.g., the hub 226 in FIG. 3B) and/or the cannula transition (e.g., the cannula transition 230 in FIG. 3B), or when the distal segment 404 has the indentation.

In certain embodiments, the infusion cannula 400 has an intermediate shaft length 450 of between about 0.050 and about 0.130 inches, such as between about 0.060 and about 0.111 inches, such as about 0.065 inches. In certain embodiments, the infusion cannula 400 has a total length 446 of between about 0.320 and about 0.400 inches, such as between about 0.325 and about 0.385 inches, such as about 0.338 inches. In certain embodiments, the infusion cannula 400 has a width 447, which may be a diameter of between about 0.080 inches and about 0.110 inches, such as about 0.092 inches. Similar to the VFC cannula 300 previously described in FIG. 3D, the segments 402, 404, and 414 and the transitions 406, 407, and 408 share a common central axis 412 disposed through a center of the infusion cannula 400, which is formed from a single, unitary body. In certain embodiments, the proximal segment 402 measures a first length 434, the intermediate segment 414 measures a second length 435, and the distal segment 404 measures a third length 436, each measured along the central axis 412. The third length 436 may be more than, less than, or equal to second length 435. In some embodiments, the third length 436 may be between about 0.020 inches and about 0.100 inches, such as between about 0.035 inches and about 0.08 inches, such as about 0.050 inches. Therefore, in some embodiments, the ratio between the third length 436 to total length 446 may be between about 0.05 and 0.25, such as about 0.050 inches/0.338 inches=0.148. In some embodiments, the ratio between the intermediate shaft length 450 to total length 446 may be between about 0.08 and 0.28, such as about 0.065 inches/0.338 inches=0.192.

In some embodiments, the total of the intermediate shaft length 450 and the third length 436 may be between about (0.05 inches+0.02 inches=0.07 inches) and about (0.130 inches+0.100 inches=0.230 inches), such as between about (0.060 inches+0.035 inches=0.095 inches) and about (0.111 inches+0.08 inches=0.191), such as about (0.065 inches+ 0.050 inches=0.115 inches). Therefore, in some embodiments, the ratio of the (total of the intermediate shaft length 450 and the third length 436) to the total length 446 may be between about 0.2 and 0.4, such as about (0.115 inches/ 0.338 inches=0.340). Note that although features are described herein with particular dimensions or ranges of dimensions, other dimensions and/or IDs are further contemplated.

As shown in FIG. 4D, the first transition 406 includes a first fillet 406A, the first chamfer 406C, and a fifth fillet 406B; the second transition 407 includes a second fillet 407A and a third fillet 407B; and third transition 408 includes a fourth fillet 408A. The fillets 406A, 406B, 407A, 407B and 408A and the chamfer 406C are formed on inner walls of the transitions 406, 407, and 408, but in further embodiments are formed on inner and/or outer walls of the transitions 406, 407, and 408. In certain embodiments, the fillets 406A, 406B, 407A, 407B and 408A are configured substantially similar to the fillets of the VFC cannula 300 previously described in FIG. 3D. In certain embodiments, the first chamfer 406C is used in lieu of first fillet 406A and/or fifth fillet 406B. In certain embodiments, the first transition 406 includes a second chamfer instead of the fifth fillet 406B. In certain embodiments, a transition angle θ (e.g., a first transition angle 452 in FIG. 4D) measures between the first chamfer 406C and an axis of one of the segments 402, 404, or 414, which may not be collinear with the central axis 412. In certain embodiments, the transition angle θ measures between the first chamfer 406C and the central axis 412. In certain embodiments, the transition angle θ is between about 150 degrees and about 170 degrees, such as about 161 degrees, but in further embodiments may be about 90 degrees and up to and including about 165 degrees. In further embodiments, the transition angle θ is more than 90 degrees. In certain embodiments, a chamfer angle α measures between the second chamfer and one of the axes previously described (e.g., the central axis 412). In certain embodiments, the chamfer angle α is greater than the transition angle θ. In certain embodiments, the walls of the segments 402, 404, and 414 are configured substantially similar to the walls of the VFC cannula 300 previously described in FIG. 3D.

In certain embodiments, the first transition 406 includes a first chamfer or bevel (e.g., a first chamfer 406C in FIG. 4D) as described in FIG. 4D. In certain embodiments, the third distal end 405B includes a sixth fillet (e.g., the fourth fillet 238 in FIG. 2D) and/or a second chamfer or bevel similar to as described in FIG. 2D. The sixth fillet and/or the second chamfer may beneficially facilitate the insertion of the VFC cannula 102 into the valved cannula 220 by gradually increasing the outer diameter of the third distal end 305B.

In certain embodiments, a second transition 407 includes a third chamfer or bevel, which is positioned in a manner similar to the first chamfer 406C but in relation to the fillets 407A and 407B.

In certain embodiments, a continuous flow path is formed between the first proximal end 403A and the third distal end 405B of the infusion cannula 400, and curvatures of the transitions enable a fluid to smoothly flow through the infusion cannula 400 by reducing fluid friction losses, thereby beneficially improving fluidic performance.

In summary, embodiments of the present disclosure include fluid cannulas for improved fluid administration and fluid flow during ophthalmic surgical procedures. For example, embodiments described herein provide efficient administration of ocular infusion fluids and tamponades, thereby facilitating improved intraocular pressure maintenance. The cannula assemblies described include embodiments wherein a smallest inner diameter (ID) of the cannula is larger than an ID of a shaft of a corresponding valved cannula. The larger cannula ID reduces overall flow resistance and pressure drop through the improved fluid cannulas which increases the flow rate at a given source pressure as described in more detail below. The cannula assemblies further include embodiments wherein the cannula includes an intermediate segment having an ID larger than the ID of the valved cannula shaft, a distal segment extending a reduced distance into the valved cannula shaft, and a smooth transition between the intermediate and distal segments. The cannula assemblies further include embodiments wherein the cannula includes a chamfer or bevel in a transition between a proximal segment of the cannula and the intermediate segment such that the transition is funnel shaped. Accordingly, the aforementioned cannulas are particularly beneficial during injection, extraction, infusion, and venting of fluids to and/or from the eye, as fluidic resistance is decreased, thus enabling less operating pressure to achieve a given flow rate.

Example Embodiments

Embodiment 1: A cannula device for a surgical procedure comprising a proximal segment comprising a first inner diameter (ID), a first proximal end, and a first distal end; a distal segment comprising a second ID smaller than the first ID, a second proximal end, and a second distal end configured to be disposed inside a hub or a cannula transition of a valved cannula comprising the hub, a shaft, and the cannula transition between the hub and the shaft.

Embodiment 2: The cannula device of Embodiment 1 described above, wherein the second distal end further comprises a fourth fillet or a second chamfer.

Embodiment 3: The cannula device of Embodiment 2 described above, wherein the fourth fillet or the second chamfer is formed on an inner or an outer wall of the distal segment.

Embodiment 4: The cannula device of Embodiment 3 described above, wherein the proximal segment and the distal segment share a common central axis of the cannula device.

Embodiment 5: The cannula device of Embodiment 3 described above, further comprising a first transition connecting the proximal segment and the distal segment via the first distal end and the second proximal end, the first transition comprising a first fillet and a second fillet.

Embodiment 6: The cannula device of Embodiment 5 described above, wherein the first fillet is concave and second fillet is convex.

Embodiment 7: The cannula device of Embodiment 5 described above, wherein the first and/or second fillet are formed on an inner or an outer wall of the first transition.

Embodiment 8: The cannula device of Embodiment 5 described above, wherein the first transition further comprises a first chamfer positioned between the first fillet and the second fillet.

Embodiment 9: The cannula device of Embodiment 8 described above, wherein the first chamfer is formed on an inner or an outer wall of the first transition.

Embodiment 10: The cannula device of Embodiment 5 described above, further comprising a second transition connecting to the first proximal end, the second transition comprising a third fillet.

Embodiment 11: The cannula device of Embodiment 10 described above, wherein the third fillet is concave or convex.

Embodiment 12: The cannula device of Embodiment 10 described above, wherein the third fillet is formed on an inner or an outer wall of the second transition.

Embodiment 13: The cannula device of Embodiment 10 described above, wherein the second transition connects the proximal segment to an adapter for a syringe or a tubing of an infusion line.

Embodiment 14: The cannula device of Embodiment 5 described above, wherein the proximal segment and the distal segment share a common central axis of the cannula device.

Embodiment 15: The cannula device of Embodiment 14 described above, wherein the first transition and/or the second transition share the common central axis of the cannula device.

Embodiment 16: The cannula device of Embodiment 14 described above, wherein the first transition further comprises a first chamfer positioned between the first fillet and the second fillet.

Embodiment 17: The cannula device of Embodiment 16 described above, wherein the first chamfer comprises a transition angle between the first chamfer and the common central axis, the transition angle measuring about 161 degrees.

Embodiment 18: The cannula device of Embodiment 5 described above, wherein the first transition further comprises a first chamfer positioned between the first fillet and the second fillet.

Embodiment 19: A cannula device for a surgical procedure comprising a proximal segment comprising a first inner diameter (ID), a first proximal end, and a first distal end; an intermediate segment comprising a second ID smaller than the first ID, a second proximal end, and a second distal end; a first transition connecting the proximal segment and the intermediate segment via the first distal end and the second proximal end, the first transition comprising a first fillet; a distal segment comprising a third ID smaller than the second ID, a third proximal end, and a third distal end; and a second transition connecting the intermediate segment and the distal segment via the second distal end and the third proximal end, the second transition comprising a third fillet and a fourth fillet.

Embodiment 20: The cannula device of Embodiment 19 described above, wherein the first fillet is concave and second fillet is convex.

Embodiment 21: The cannula device of Embodiment 19 described above, wherein the first transition further comprises a second chamfer or a second fillet.

Embodiment 22: The cannula device of Embodiment 21 described above, wherein the first transition further comprises a first chamfer positioned between the first fillet and the second chamfer or second fillet.

Embodiment 23: The cannula device of Embodiment 22 described above, wherein the proximal segment and the distal segment share a common central axis of the cannula device.

Embodiment 24: The cannula device of Embodiment 23 described above, wherein the first chamfer comprises a transition angle between the first chamfer and the central axis of the device, the transition angle measuring between about 90 and about 165 degrees.

Embodiment 25: The cannula device of Embodiment 19 described above, further comprising an internal shaft length of between about 0.050 and about 0.098 inches.

Embodiment 26: The cannula device of Embodiment 21 described above, wherein the first fillet, the second fillet, and/or the second chamfer are formed on an inner or an outer wall of the first transition.

Embodiment 27: The cannula device of Embodiment 21 described above, wherein the first transition further comprises a first chamfer positioned between the first fillet and the second fillet.

Embodiment 28: The cannula device of Embodiment 27 described above, wherein the first chamfer is formed on an inner or an outer wall of the first transition.

Embodiment 29: The cannula device of Embodiment 19 described above, wherein the third fillet is concave and fourth fillet is convex.

Embodiment 30: The cannula device of Embodiment 19 described above, wherein the third and/or fourth fillet are formed on an inner or an outer wall of the second transition.

Embodiment 31: The cannula device of Embodiment 19 described above, further comprising a third transition connecting to the first proximal end, the third transition comprising a fifth fillet.

Embodiment 32: The cannula device of Embodiment 31 described above, wherein the fifth fillet is concave or convex.

Embodiment 33: The cannula device of Embodiment 31 described above, wherein the fifth fillet is formed on an inner or an outer wall of the third transition.

Embodiment 34: The cannula device of Embodiment 31 described above, wherein the third transition connects the proximal segment to an adapter for a syringe or a tubing of an infusion line.

Embodiment 35: The cannula device of Embodiment 19 described above, wherein the third distal end is configured to be disposed inside a valved cannula having a hub and a shaft, wherein at least a portion of the distal segment is configured to frictionally engage with an inner surface of the valved cannula.

Embodiment 36: The cannula device of Embodiment 35 described above, wherein at least a portion of the intermediate segment is configured to frictionally engage with an inside of the hub of the valved cannula.

Embodiment 37: The cannula device of Embodiment 35 described above, wherein at least a portion of the intermediate segment is configured to frictionally engage with an indentation inside of the valved cannula.

Embodiment 38: The cannula device of Embodiment 19 described above, wherein the proximal segment, the distal segment, the first transition, and/or the second transition share a common central axis of the cannula device.

Embodiment 39: The cannula device of Embodiment 31 described above, wherein the proximal segment, the distal segment, the first transition, the second transition, and/or the third transition share a common central axis of the cannula device.

Embodiment 40: The cannula device of Embodiment 19 described above, wherein the third distal end further comprises a sixth fillet or a second chamfer.

Embodiment 41: The cannula device of Embodiment 40 described above, wherein the sixth fillet or the second chamfer is formed on an inner or an outer wall of the distal segment.

The preceding description is provided to enable any person skilled in the art to practice the various embodiments described herein. The examples described herein are not limiting of the scope, applicability, or embodiments set forth in the claims. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, the word "exemplary" means "serving as an example, instance, or illustration." Any aspect described herein as "exemplary" is not necessarily to be construed as preferred or advantageous over other aspects.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

The following claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112(f) unless the element is expressly recited using the phrase "means for" or, in the case of a method claim, the element is recited using the phrase "step for." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. A cannula device system for a surgical procedure comprising:
    a valved cannula comprising a hub, a shaft, and a cannula transition between the hub and the shaft;
    a viscous fluid control (VFC) cannula, comprising:
        a proximal segment comprising a first inner diameter (ID), a first proximal end, and a first distal end; and
        a distal segment comprising a second ID smaller than the first ID, a second proximal end, and a second distal end terminating inside the hub of the valved cannula, wherein a gap is formed between the distal segment and the hub sufficient to allow injected fluid to backflow out of the valved cannula when a pressure in an eye is higher than a pressure exerted on the injected fluid;
    wherein the proximal segment and the distal segment have a common central axis disposed through a center of the VFC cannula;
    wherein a first transition connecting the proximal segment and the distal segment via the first distal end and the second proximal end comprises a first concave fillet and a second convex fillet;
    wherein a ratio of a length of the distal segment to a total length of the VFC cannula is approximately in a range of 0.2 to 0.4; and
    wherein a positional angle between the central axis and a tangential line through a midpoint of the first concave fillet is approximately in a range of 20 and 40 degrees.

2. The cannula device system of claim 1, wherein the ratio of the length of the distal segment to the total length of the VFC cannula is approximately 0.325.

3. The cannula device system of claim 1, wherein the positional angle of the VFC cannula is approximately 26 degrees.

4. The cannula device system of claim 1, wherein the shaft of the valved cannula has a third ID smaller than the second ID.

5. The cannula device system of claim 1, wherein at least a portion of the distal segment of the VFC cannula is configured to frictionally engage with an inner surface of the valved cannula.

6. The cannula device system of claim 5, wherein the distal segment of the VFC cannula is configured to frictionally engage with an inner surface of the hub or the cannula transition of the valved cannula.

7. The cannula device system of claim 1, wherein the VFC cannula further comprises a second transition connecting to the first proximal end, the second transition comprising a third fillet.

8. The cannula device system of claim 1, wherein the second distal end of the VFC cannula comprises a fourth fillet or second chamfer.

* * * * *